(12) United States Patent
Fregonese

(10) Patent No.: US 9,821,014 B2
(45) Date of Patent: Nov. 21, 2017

(54) COMPOSITIONS BASED ON CLAY AND BEEPOLLEN, METHOD FOR PREPARING SAME AND NUTRITIONAL AND THERAPEUTIC USES THEREOF

(75) Inventor: Alexandra Fregonese, Moncaut (FR)

(73) Assignee: Laboratoire Beepratte, Paris (FR)

( * ) Notice: Subject to any disclaimer, the term of this patent is extended or adjusted under 35 U.S.C. 154(b) by 632 days.

(21) Appl. No.: 13/993,182

(22) PCT Filed: Dec. 14, 2011

(86) PCT No.: PCT/EP2011/072756
§ 371 (c)(1),
(2), (4) Date: Jul. 8, 2013

(87) PCT Pub. No.: WO2012/080333
PCT Pub. Date: Jun. 21, 2012

(65) Prior Publication Data
US 2013/0287855 A1    Oct. 31, 2013

(30) Foreign Application Priority Data
Dec. 14, 2010 (FR) ...................... 10 60511

(51) Int. Cl.
| | | |
|---|---|---|
| *A61K 9/14* | (2006.01) | |
| *A61K 35/64* | (2015.01) | |
| *A61K 8/26* | (2006.01) | |
| *A61K 8/97* | (2017.01) | |
| *A61K 33/06* | (2006.01) | |
| *A61K 35/02* | (2015.01) | |
| *A61Q 19/00* | (2006.01) | |
| *A23L 21/20* | (2016.01) | |
| *A23L 33/16* | (2016.01) | |

(52) U.S. Cl.
CPC ............ *A61K 35/642* (2013.01); *A23L 21/20* (2016.08); *A23L 33/16* (2016.08); *A61K 8/26* (2013.01); *A61K 8/975* (2013.01); *A61K 33/06* (2013.01); *A61K 35/02* (2013.01); *A61K 35/64* (2013.01); *A61Q 19/00* (2013.01); *A23V 2002/00* (2013.01)

(58) Field of Classification Search
CPC .... A61K 2300/00; A61K 33/06; A61K 35/02; A61K 35/64; A61K 35/642; A61K 8/26; A61K 8/975; A61Q 19/00
See application file for complete search history.

(56) References Cited

U.S. PATENT DOCUMENTS

| | | | | |
|---|---|---|---|---|
| 6,071,539 A | * | 6/2000 | Robinson et al. ............ | 424/466 |
| 2002/0012640 A1 | | 1/2002 | Mohammadi et al. | |
| 2008/0031940 A1 | | 2/2008 | Rodriguez | |
| 2008/0219939 A1 | | 9/2008 | Grune | |

FOREIGN PATENT DOCUMENTS

| | | | | |
|---|---|---|---|---|
| CN | 1806574 A | | 7/2006 | |
| CN | 1965799 | | 5/2007 | |
| CN | 101415441 A | * | 4/2009 | ........... A61K 31/201 |
| CN | 101711799 A | | 5/2010 | |
| EP | 0 191 128 A1 | | 8/1986 | |
| JP | S59-213369 | | 12/1984 | |
| RU | 2113806 C1 | * | 6/1998 | ............... A23L 1/30 |
| RU | 2372893 C2 | * | 11/2009 | ........... A61K 9/2077 |
| WO | WO 2005041934 A2 | * | 5/2005 | ........... A61K 9/2077 |
| WO | WO 2007/075972 A2 | | 7/2007 | |
| WO | WO 2008/109182 A1 | | 9/2008 | |

OTHER PUBLICATIONS

Holistic Serums, Pomegranate and bee pollen scrub, Retrieved online [Mar. 9, 2015], Retrieved from URL:<https://web.archive.org/web/20100327032343/http://www.holisticserums.com/carenew/masques.shtml>.*
Bee Source, Retrieved on [Dec. 28, 2015], Retrieved from URL:<http://www.beesource.com/forums/showthread.php?194965-how-to-dry-pollen>.*
Raul Costa-Pereira, Removal of clay by stingless bees: load size and moisture selection, Annals of the Brazilian Academy of Sciences, 2014, pp. 1287-1293.*
Eraslan, G., et al., Evaluation of protective effect of bee pollen against propoxur toxicity in rat, Ecotoxicology and Environmental Safety, 2009, pp. 931-937, No. 72.
Georgiev, D.B., et al., Effects of an Herbal Medication Containing Bee Products on Menopausal Symptoms and Cardiovascular Risk Markers: Results of a Pilot Open-uncontrolled Trial; MedGenMed, Dec. 16, 2004,6(4):46.
Wilt, T., et al., Cernilton for benign prostatic hyperplasia (Cochrane Review), 2002, Issue 4.
Wu, Y-D, et al., A Steroid Fraction of Chloroform Extract from Bee Pollen of *Brassica campestris* Induces Apoptosis in Human Prostate Cancer PC-3 Cells, Phytother, 2007, 1087-1091, Res. 21.
Yamaguchi, M., et al., Anabolic Effects of Bee Pollen *Cistus ladaniferus* Extract on Bone Components in the Femoral-Diaphyseal and -Metaphyseal Tissues of Rats in Vitro and in Vivo, J. Health Science, 2006, pp. 43-49, 52(1).
International Search Report (PCT/ISA/210) issued on Feb. 1, 2012, by the European Patent Office as the International Searching Authority for International Application No. PCT/EP2011/07256.
Written Opinion (PCT/ISA/237) issued on Feb. 1, 2012, by the European Patent Office as the International Searching Authority for International Application No. PCT/EP2011/07256.
Machkovskiy M.D., Médicaments (1977).

* cited by examiner

*Primary Examiner* — Nannette Holloman
(74) *Attorney, Agent, or Firm* — Buchanan Ingersoll & Rooney PC

(57) ABSTRACT

The present invention relates to complexes of beepollen and clay, as well as to their preparation methods and to their therapeutic uses or as a food supplement, a functional food, in human and animal healthcare.

15 Claims, 3 Drawing Sheets

Figure 1:
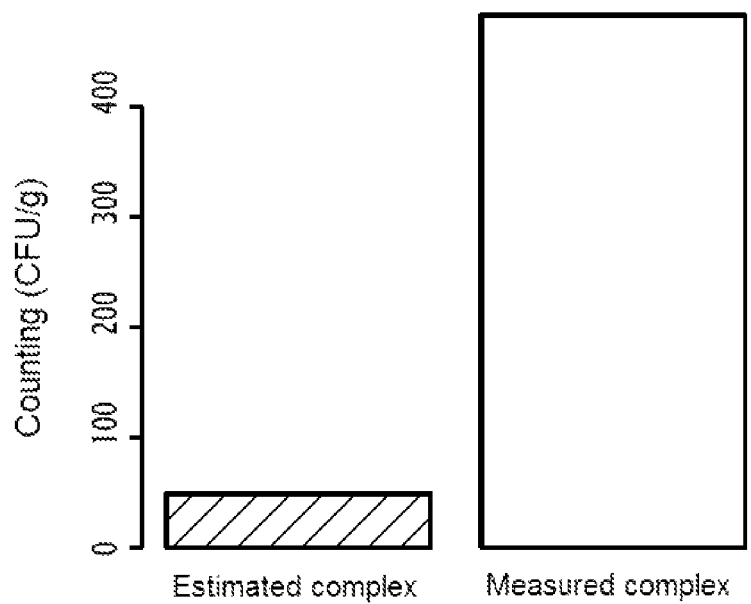

COMPOSITIONS BASED ON CLAY AND BEEPOLLEN, METHOD FOR PREPARING SAME AND NUTRITIONAL AND THERAPEUTIC USES THEREOF

Pollen is the male pollinating element of flowers and represents the only source of protein for bees. It is collected by the bee from the male organ of the flower in order to be transported to the hive in the form of small balls. It is then often designated by the term of <<beepollen>> in order to distinguish this pollen conveyed by the bees from the one conveyed by winds. Thus harvested by the bee, beepollen is enriched with probiotic elements, such as ferments and yeasts, contained in the saliva of the bee.

Because of its intrinsic structure, pollen is also a highly interesting foodstuff in human nutrition since fresh pollen consists of proteins (±25%) notably including amino acids which are indispensable for the body, including those which it cannot synthesize (phenylalanine, tryptophan, tyrosine, lysine, threonine, methionine, cysteine, leucine, isoleucine, valine) and enzymes and coenzymes (including amylase, invertase, phosphatase, transferases); vitamins present in a large number: the totality of the vitamins of group B, vitamin C, vitamin D, provitamin A, vitamins K, E, rutin; trace elements such as calcium, magnesium, phosphorus, iron, copper, manganese . . . '; minerals; (copper, iron, manganese, phosphorus, silicon, sulfur); sterols; flavonoids; pigments; estrogenic substances; growth factors; selenium; carbohydrates; lipids, etc. Because of the significant nutritional benefits, pollen has an extended metabolic action and gives vitality for best general fitness.

For example, the richness of pollen in phytoestrogens such as isoflavones allows protection against cardiovascular diseases, osteoporosis, prostate cancer. The presence of flavonoids in pollen also suggests a beneficial effect on body liquid flow.

More particularly, the effect on osteoporosis is also supported by bone stimulation in rats induced by oral intake of pollen (Yamaguchi et al. J. of Health Science 2006, 43-49).

Several studies have also shown the efficiency of pollen (Cernilton®, a standardized mechanically harvested pollen extract of rye) in the treatment of benign hyperplasia of the prostate (Wilt et al. Cochrane Database Syst. Rev. 2000 (2) CD001042). The activity of different beepollen extracts on certain types of prostate cancers by cell apoptosis has also been reported (Wu et al. Phytother. Res. 2007, 21(11), 1087-1091).

Eraslan et al. (Ecotoxicol. Environ. Saf 2009, 72(3), 931-937) have described the protective effect of beepollen during administration of a hepatotoxic agent, suggesting the beneficial effect of beepollen on the liver and generally on metabolism.

Improvement of menopausal symptoms has been observed upon administration of a composition based on pollen (Georgiev et al., Med. Gen. Med. 2004, 6(4), 46).

It has also been recognized that pollen restores nervous balance, and improves insomnia and fatigue conditions. Pollen is also sought for stimulating gastric functions (with favorable effects on appetite, digestion and regulation of the digestive transit) and for circulatory disorders. Thus, pollen contributes to blood regeneration, notably by increasing the hemoglobin level and it would therefore be particularly indicated in anemic persons or children; it also regulates blood coagulation (antithrombin) and contributes to cardiovascular protection by the combination of arterio-capillo-venous resistance and elasticity agents: rutin, vitamin C and E and methionine. The presence of vitamin A also suggests a beneficial effect of pollen on preventing or treating ocular disorders.

In addition to these intrinsic benefits of pollen, beepollen, if it is delivered intact in the intestine, many allow the administration of lactic ferments contributing to the intestinal flora essential for health.

However, fresh pollen is not stable. Thus, today, pollen is essentially marketed in two forms.

In a dry form which facilitates its distribution (long life, easy to use), pollen nevertheless loses the main part of its notably antibacterial properties.

The frozen form gives the possibility of maintaining the properties of pollen but makes marketing and the taking by the patient not very convenient, because of the cold chain which has to be maintained.

Either dry or frozen, pollen appears in the form of grains, having other drawbacks, such as the difficulty of observing a real dosage and a taste which may be estimated as unpleasant, both for the final consumers and for carrying out clinical studies.

It is therefore desirable to make available a formulation allowing administration of beepollen in a preferably natural form, in which it has preserved the properties of fresh beepollen, notably the aforementioned nutritional and physiological properties, while meeting requirements of stability and of ease of use.

The present inventors have, from now on, demonstrated synergies between beepollen and clay allowing stable formulation of beepollen and preservation or even optimization of the nutritional, physiological and therapeutic properties thereof, promotion of its preservation, its administration, its placement on the market, its consumption and its assimilation and the carrying out of clinical studies.

Thus, the present invention relates to combinations of beepollen and of clay. Said combinations allow formulation of beepollen while meeting the aforementioned requirements.

Because of the absorption, retention and adsorption properties of clay, the thereby formed combination has an intimately related structure and may also be designated here as a <<beepollen/clay complex>>.

The beepollen/clay complexes according to the invention may also be defined as any stable material resulting from the binding of beepollen stemming from any plant species on a silicate lamellar structure.

In the sense of the invention, by <<beepollen>> is meant pollen sampled after having been harvested by bees. It may be sampled with any means notably just before its entry into the hive (by means of a pollen trap) or in the hive according to customary methods.

The term of <<beepollen>> designates pollen in any form allowing the biological activity of fresh pollen to be maintained. It therefore comprises fresh beepollen as well as notably beepollen which has been frozen beforehand.

Within the scope of the present invention, beepollen may originate from various plant species and varieties and is not limited to a particular flower. Mention may thus be made of beepollen from rye, maize, sun flower, cist, chestnut, kiwi, willow, poppy, lavender, heather . . .

Beepollen, notably frozen beepollen may be commercially available for example at Pollenergie.

Beepollen may also be of variable composition, notably depending on the nature of the original plants as well as on the period of the harvesting or further on the harvesting method.

Thus, fresh beepollen suitable for the invention generally contains 5% to 36% of water and 64% to 95% of dry materials, from the latter:
- 2.5% to 3.8% of mineral salts;
- 4.2% to 19.8% of lipids;
- 8% to 30% of albumin;
- 5% to 7% of starch;
- vitamins;
- growth factors;
- folic acid;
- polyphenols;
- phytosterols;
- ferments and yeasts.

By <<clay>> is meant a material comprising clay minerals such as silicate hydrates, notably aluminum or magnesium silicates. Phyllosilicates are notably preferred which have a lamellar structure consisting of one or several lamellas.

According to the Jozja classification, based on the thickness and the structure of the lamellas, four groups of clays are distinguished:
i) 7 Å minerals: Its thickness is of about 7 Å, this is the category of kaolinites (kaolin, halloysite . . . )
ii) 10 Å minerals: Its thickness is of about 10 Å, this is the category of illites (illite, glauconite, . . . )
iii) 14 Å minerals: Its thickness is of about 14 Å, this is the category of smectites (montmorillonite, bentonite, ghassoul . . . )
iv) Fibrous minerals: The thickness of the lamella is variable, they are called chlorites or fibrous minerals (sepiolite, attapulgite . . . )

The term of <<clay>> according to the invention therefore refers to these four types of clay. As clay minerals, mention may notably be made of illite, chlorite, glauconite, kaolinite, attapulgite, sepiolite and montmorillonite. As a clay, are notably preferred, kaolin, illit, montmorillonite, attapulgite, and more particularly montmorillonite.

Clay materials have specific physico-chemical characteristics such as a negative electric charge, which has to be compensated by cations located in the interfoliar spaces. The cationic exchange capacity (CEC) is specific to the type of clay materials. The CEC is defined as the number of monovalent or equivalent cations which may be substituted for the compensating cations in order to compensate the negative charge of 100 g of clay. It is determined by gradual introduction of a colored reagent (cations) in an aqueous suspension until saturation. The CEC is generally expressed in mequiv./100 g.

The lamella structure also leads to the specific property of clay materials, that of swelling in the presence of water. The swelling corresponds to the penetration of water molecules into the interfoliar space and may be of the crystalline type (rupture of the electrostatic forces between the charged lamellas and the cations in the presence of water) or of the osmotic type (formation of a gel and then of a suspension in presence of a more significant amount of water).

Thus, the different aforementioned types of clay having CECs and specific absorption capacities, thus montmorillonite has a CEC comprised between 80 and 150 mequiv./100 g and an absorption capacity (a property measured by the weight difference between dry clay and humid clay) of the order of 20%.

The complexes according to the invention generally comprise:
- from 4% to 90% of beepollen, and
- from 10% to 96% of clay.

The percentages are by weight.

More preferentially, the complexes according to the invention comprise:
- from 20% to 40% of beepollen and
- from 60% to 80% of clay, and more particularly:
- from 30% to 35% of beepollen and
- from 65% to 70% of clay.

With the complexes according to the invention, it is possible to maintain the beepollen in a form in which it retains its biological activity. With the complexes according to the invention, it is therefore possible to maintain sufficient humidity in order to preserve the ferments and yeasts, while allowing for, and this unexpectedly, the stability of the thereby formulated beepollen.

The complexes according to the invention advantageously have a grain size of less than 500 μm, a humidity level of less than 15% and/or a water activity (wa) of less than 0.75.

According to another object, the present invention also relates to the method for preparing the complexes according to the invention. Thus, said method comprises the step for mixing beepollen and clay.

The mixing is advantageously achieved with stirring in ambient air. Generally, the complexes are prepared by making sure that no contamination by water (in liquid form) is possible during the making of the mixture (totally dry material).

The desired grain size is obtained by means of a sieve with meshes of 500 μm.

According to the present invention, the complexes have a specific biological activity related to the beepollen used, and potentialized by the clay; conversely, the clay has intrinsic properties such as the action protecting the intestinal mucosa, its anti-acid and anti-alkaline powers, its capacity of binding and discharging gases and toxins.

By <<biological activity>> is meant here the nutritional or physiological effect such as a therapeutic effect, exerted by said complexes in subjects which have consumed them.

Beepollen is actually known for its nutritional properties as a concentrated source of nutrients and its physiological properties on osteoporosis, cardio-vascular diseases, the liver and metabolism, circulatory disorders, menopausal symptoms, the nervous system, the gastro-intestinal system, articular, ocular, urinary disorders, fatigue, prostate disorders such as benign hypertrophy of the prostate, chronic prostatitis, prostatodynia and prostate cancer, etc. It is also useful for its properties in nutrition, dermatology and cosmetodermatology, including appendages (nails, hair), asthenia and fatigability, convalescence and post-surgery, hydro-electrolytic imbalances, improvements in physical conditions.

Thus, the inventors have shown that synergies applied by beepollen/clay complexes and notably the capacity and rate of absorption of the complex, its retention capacity, its adsorption capacity, its load of lactic ferments and its effect on microorganisms, which are generally greater than the sum of the effects of each of its constituents.

Potentialization of these properties gives the possibility of contemplating improvement in the effects of beepollen and/or of clay, thereby administered within a complex according to the invention.

The complexes according to the invention are therefore useful on a therapeutic or nutritional basis, for human and/or animal use, and for preventive and/or therapeutic use.

The present invention therefore also relates to a pharmaceutical composition comprising a complex according to the invention.

Said composition may thus notably form a pharmaceutical specialty in the sense of the European Directive 2001/83/EC.

Said composition may also comprise one or several pharmaceutically acceptable excipients.

The pharmaceutical compositions according to the invention may appear in forms intended for administration via an oral, sublingual, topical, local, intratracheal, intranasal or rectal route.

They may notably be present in the form of solutes or multi-dose flasks, or in the form of exposed or coated tablets, dragees, capsules, soft and hard gelatin capsules, granules, pills, tablets, powders, suppositories or rectal capsules, solutions or suspensions, or further creams, gels, ointments, patches, etc.

The pharmaceutically acceptable excipients which are suitable for such administrations may notably be selected from derivatives of cellulose or of microcrystalline cellulose, earth alkaline carbonates, magnesium phosphate, starches, modified starches, lactose for solid forms, cocoa butter or polyethylene glycol stearates, water, aqueous solutes, saline, isotonic solutes, etc.

The present invention is more particularly directed to gelatin capsules comprising a beepollen/clay complex.

The formulation of such gelatin capsules may be carried out according to customary practice.

Preferably, said composition contains an effective amount of the complex according to the invention.

The dosage may vary within wide limits (0.5 mg to 1000 mg) depending on the therapeutic indication and on the administration route, as well as on the age and weight of the subject.

There may be particular cases where higher or lower doses are suitable: such dosages do not depart from the scope of the invention. According to customary practice, the suitable dosage for each patient is determined according to the administration method, the weight and the response of said subject.

The present invention also relates to a complex according to the invention for use in preventing and/or treating osteoporosis, cardio-vascular diseases, cancers, liver and metabolism disorders, fatigue, circulatory disorders, articular disorders, menopausal symptoms, disorders of the nervous system, disorders of the gastrointestinal system, ocular, urinary disorders, prostate disorders such as benign hypertrophy of the prostate, chronic prostatitis, prostatodynia and prostate cancer, nutritional, dermatological and cosmetodermatological disorders, asthenia and fatigability, convalescence and post-surgery, hydro-electrolytic imbalances, improvement in physical conditions, etc.

According to another object, the present invention also relates to the use of a complex according to the invention, as a nutrient.

By <<use as a nutrient>> is meant the use of a complex according to the invention like or in a functional food (or nutraceutical) or food supplement.

Functional foods or nutraceuticals are generally defined as a conventional food, or which has the aspect thereof, which belongs to normal feeding, and which has the characteristic of providing beneficial physiological effects exceeding its customary nutritional functions or of reducing the risk of chronic diseases.

Said supplement may thus form a food supplement in the sense of the European Directive 2002/46/EC.

Indeed, the complexes according to the invention form a foodstuff, the purpose of which is to complete a normal food diet by forming a concentrated source of nutrients (notably the aforementioned vitamins B, provitamin A and vitamins C, D and E, and minerals) and the other aforementioned substances having a nutritional and/or physiological effect as a combination.

The present invention therefore relates to a food composition, such as a functional food or a food supplement comprising a beepollen/clay complex according to the invention.

Said food supplement is advantageously formulated as a dose, i.e. in a dosage form defined by the European Directive 2002/46/EC, such as <<gelatin capsules, lozenges, tablets, pills and other similar forms as well as powder sachets, liquid ampules, flasks provided with a dropper and other similar forms of liquid or powder preparations intended to be taken in units of small amounts>>.

The food supplement according to the invention advantageously appears in the form of gelatin capsules. It may also comprise conventional food excipients.

The present invention also relates to the combinations comprising a beepollen/clay complex according to the invention with another active agent.

The beepollen/clay complexes according to the invention may actually be useful for potentializing the common activity of said agent and of the complex, or as a carrier for improving the formulation, administration and/or bioavailability, or further for reducing secondary effects thereof.

Thus, the present invention also relates to a drug comprising as a carrier, a clay and beepollen combination according to the invention.

FIGS. 1 to 6 respectively illustrate the load of lactic bacteria, of fungi, and the absorption capacity, absorption rate, retention power and capacity of adsorbing a beepollen/clay complex according to the invention, as compared with a value estimated on the basis of the properties of each of its ingredients.

The following examples illustrate the invention, without however limiting it. The initial products used are products which are known or prepared according to known operating procedures.

The percentages are expressed by weight, unless indicated otherwise.

EXAMPLE 1

Preparation of Beepollen/Clay Complexes

Hardware:
Precision electronic scales—Mettler Toledo PG803
Stirrer—IKA Labotechnik Eurostar
Glass beaker 250 mL—Bomex
Spoon-shaped curved spatula, in stainless steel 18/8—Labo-moderne
Suppliers of Raw Materials:
Sunflower beepollen frozen under nitrogen gas: Pollenergie, La Grabère—47450 Saint-Hilaire de Lusignan; Tel. 05 53 68 11 11—Fax. 05 53 68 11 12
Montmorillonite clay, Argiletz, 14 route d'Echampeau—77 440 Liz-sur-Ourcq, Tel. 01 60 61 20 88—Fax. 01 60 61 27 39.
9 different compositions (%) of the complex were made:
100 clay/0 beepollen,
90 clay/10 beepollen,
80 clay/20 beepollen,
66.66 clay/33.33 beepollen,
50 clay/50 beepollen,
33.33 clay/66.66 beepollen,
20 clay/80 beepollen, 10 clay/90 beepollen,
0 clay/100 beepollen.

The illustrative operating procedure is described in more detail hereafter:

For preparing 150 g of beepollen/clay complex: the proportion of each of the components is 66.66% of clay for 33.33% of beepollen.

Weigh 100 g of clay in a 250 mL beaker;
Weigh 50 g of frozen beepollen in a 250 mL beaker;
The parts of the stirrer are preferably dried in order to avoid hydration of the complex;
Mix the clay;
Add the beepollen and leave mixing on for 30 seconds.

The desired grain size is obtained by sifting by means of a sieve with a mesh of 500 μm.

If a threshold is placed at 10% of the maximum effect, a window is determined in which the complexes have a significant effect, corresponding to:
beepollen: from 4.5% to 87.6% with preference for 33.33%;
clay from 95.5% to 12.4% with preference for 66.66%.

The thereby prepared complexes were characterized. Their product characteristics may be summarized in the table hereafter:

| ANALYSES | SPECIFICATIONS |
| --- | --- |
| Aspect | Powder |
| Color | Grey-green |
| Odor | Specific |
| Taste | Bitter |
| Texture | Granular |
| Grain size | Less than 500 μm |
| Foreign bodies | Absent |
| Density | NA |
| Ph | NA |
| Humidity | Less than 15% |
| Wa | Less than 0.75 |
| Viscosity | NA |
| Energy value | 50 kcal/100 g< <400 kcal/100 g |
| Lipids | 1%< <5% |
| Carbohydrates | 15%< <28% |
| Proteins | 3%< <11% |

Tests for evaluating the efficiency of the complex on the synergy of the components were conducted. The composition with 66.66% of clay and 33.33% of beepollen has maximum efficiency.

EXAMPLE 2

Study of the Properties of the Beepollen/Clay Complex of Example 1

Counting the Total Lactic Bacteria

The species of lactic bacteria contained in the beepollen are not clearly identified. The test which gave the possibility of counting the largest majority of the species of lactic bacteria (ISO 15214 standard) was therefore used.
Lactic bacteria of the ingredients (clay and beepollen): In order to evaluate the advantages of the beepollen/clay complex, the arbitrary amount of lactic bacteria of each of the ingredients was estimated first of all.
The clay has 0 CFU/g.
The beepollen has 152 CFU/g.
Lactic bacteria of the beepollen/clay complex: By means of the specific counting on beepollen and clay, the amount of lactic bacteria of the complex (by taking into account the clay and beepollen proportion of the complex) was therefore estimated (FIG. 1).

Thus, the beepollen/clay complex should, according to our estimation contain 50.7 CFU/g.

Now, the measurements show that the beepollen/clay complex contained 481 CFU/g.

The complex has 9.5 times more lactic bacteria than the estimation.

Development of Fungi

Fungus is an ambiguous vernacular name which designates certain filamentary microscopic microorganisms from the kingdom of mycetes. There exist thousands of different varieties of them. They are pluricellular organisms which may attain up to 35 meters in length.

Figure 2:
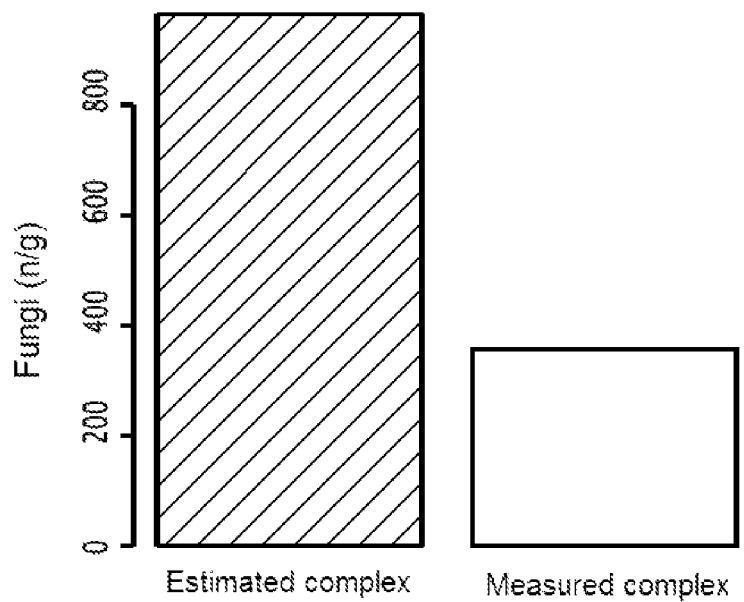

Some fungi are sources of food intoxication by the mycotoxins which they secrete (patulin, etc.).
Fungi of the ingredients (clay and beepollen): In order to evaluate the advantages of the beepollen/clay complex, the amount of fungi from each of the ingredients was estimated first of all.
The clay has 0 fungus/g.
The beepollen has 2,900 fungi/g.
Fungi of the beepollen-clay complex: By the specific counting on beepollen and on clay, the amount of fungi of the complex (by taking into account the clay and beepollen proportion of the complex) was estimated (FIG. 2).

Thus, the beepollen/clay complex should, according to this estimation, contain 967 fungi/g. Now, measurements show that the beepollen/clay complex contained 350 fungi/g.

Absorbing Power of the Beepollen/Clay Complex

The absorbing power was measured according to the following procedure:
1) Place a filter on a beaker containing water. The water gradually moistens the filter which is only slightly immersed in the water.
2) Delicately deposit the clay (or the beepollen or the complex) on the paper filter. The directly deposited material in contact with the paper filter absorbs water.
3) By capillarity, the absorption of water is gradually achieved towards the center of the deposited material.
4) The clay becomes completely impregnated with water. The weight difference between dry clay and humid clay gives the absorption capacity of the clay.

In a first phase, the absorption capacity of each of the ingredients was measured:
the clay has the capacity of absorbing 74.38% of its weight;
the beepollen has the capacity of absorbing 19.46% of its weight.

Figure 3:
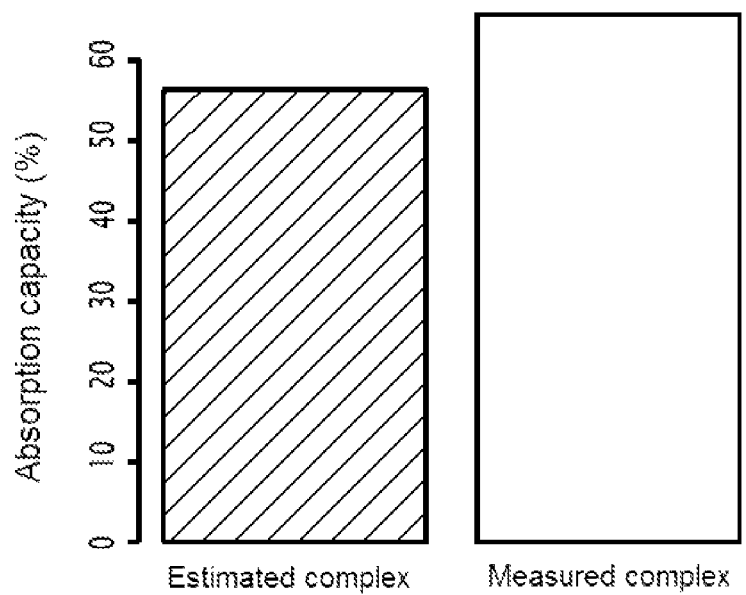

By measuring the specific absorption capacity of the beepollen and of the clay, the absorption capacity of the complex was estimated by taking into account the clay and beepollen proportion of the complex. Thus, the beepollen-clay complex should, according to this estimation, absorb 56% of its weight. Now, the measurement shows that the beepollen-clay complex absorbs 65.5% of its weight. The beepollen-clay complex therefore has an absorbing power which is 9.5% greater than the estimation (FIG. 3).

Figure 4:
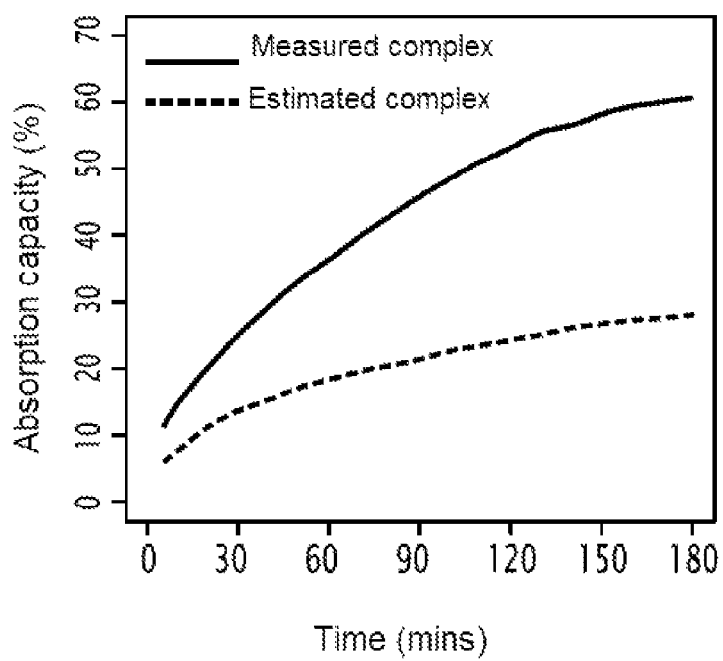

The absorption rate was also measured for each of the ingredients at different times after putting them in contact with water and by evaluating at different points, the slope of the curve. Thus, the clay has a greater absorption rate than the beepollen. By measuring the specific absorption rate of the beepollen and of the clay, the absorption capacity of the complex at different measured times was estimated by taking into account the clay and beepollen proportion of the complex. The measurements conducted with the complex show that the beepollen/clay complex absorbs water faster than the estimation stemming from the sum of both ingredients (within two hours of time, the absorbed percentage is 2.2 times greater), and also faster than clay alone (within two hours of time, the absorbed percentage is 1.8 times greater). Therefore there is a synergistic effect of the beepollen and of the clay on the absorption capacity (FIG. 4).

Retention Capacity of the Beepollen/Clay Complex

In order to evaluate the retention capacity (the products, clay, beepollen and complex) were left to absorb the maximum of water. Thus, the volume of absorbed water for each product (corresponding to the values obtained during the absorption measurement) was determined, and then the products were left to naturally dehydrate (controlled room temperature and humidity level) and the water loss was calculated (percentage relatively to the absorbed volume). The results show that:

beepollen dehydrates more rapidly than clay;
clay completely (and only) loses the water that it has absorbed while beepollen not only loses the absorbed water but also the water contained in the beepollen grain.

Figure 5:
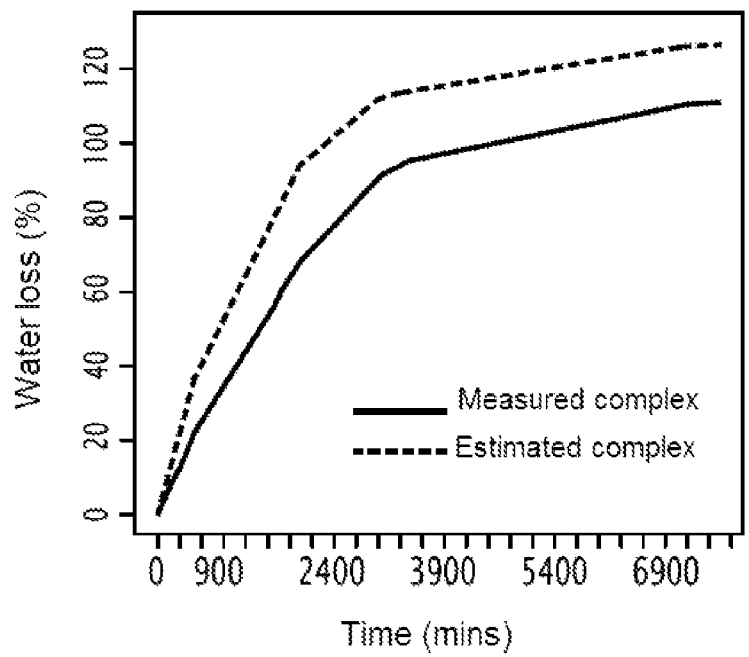

After maximum absorption, the material was withdrawn from the contact with water. The water loss is then measured at different times and illustrated as a percentage of maximum absorbed water. By the measurements of the water retention capacities for the different ingredients, the retention capacity of the beepollen-clay complex was estimated. The measurements obtained experimentally with the complex show a more significant retention power than the one estimated considering the respective proportions and capacities of its components. The complex retains liquids better than the estimation (FIG. 5).

After more than 5 days at room temperature (controlled humidity), the complex retains 15% of its weight in addition to what is expected. The formulation of beepollen and of clay gives the possibility of obtaining a product for which the retention capacity is potentialized. These characteristics show the possibility of adding products which will be preserved in the final product.

Adsorption Capacity

The adsorbing power may be determined by gradual introduction of a colored reagent (cation) into an aqueous suspension of clay until saturation. A methylene blue test was conducted: it is a colored cation which was adsorbed preferentially by clays of the montmorillonite type. It is a test commonly used in geotechnics for determining the cleanliness of a sol and the clay proportion which it contains (NF P 94-068).

The test is carried out by successively adding doses of a methylene blue solution into an aqueous suspension of clay and by checking the adsorption of the colored solution by a spot test on a paper filter in order to detect the presence of free coloring agent. Methylene blue has the property of being rapidly adsorbed by clay. As long as the methylene blue is adsorbed, it does not color the water of the solution. This is checked by depositing a drop on a paper filter: the center of the spot is bright blue (a clay having adsorbed the blue) and the halo of the spot remains colorless. From a certain dose of methylene blue, the halo also becomes colored: this is the sign that all the clay has depleted its adsorption capacity (saturation). The consumed amount of blue is therefore an indication of the adsorption capacity of the tested product. The blue value is expressed by the amount of blue in consumed grams per gram of product.

3 g of clay (montmorillonite) are homogenized in 20 mL of demineralized water. Successive additions of 1 mL of 10 g/L methylene blue solution are performed until saturation. The saturation corresponds to the moment when a blue halo is formed on the paper filter; the result is confirmed by repeating the spot test every minute for 5 minutes without adding any methylene blue solution.

It is noted that the blue halo slightly persists from an addition of 19 mL of methylene blue. By taking this value, it is possible to determine the blue value of clay as being 63.6 mg of blue/g of clay.

3 g of beepollen are homogenized in 20 mL of demineralized water. As the beepollen does not have any adsorbing properties, successive additions of 0.1 mL (and then of 1 mL starting from 1 mL) of 10 g/L methylene blue solution are performed. The saturation corresponds to the moment when a blue halo is formed on the paper filter; the result is confirmed by repeating the spot test every minute for 5 minutes without adding any methylene blue solution. The blue halo slightly persists as soon as 0.1 mL of methylene blue are added. Therefore, the beepollen does not have any adsorbing capacity (0 mg of blue/g of beepollen).

Figure 6:
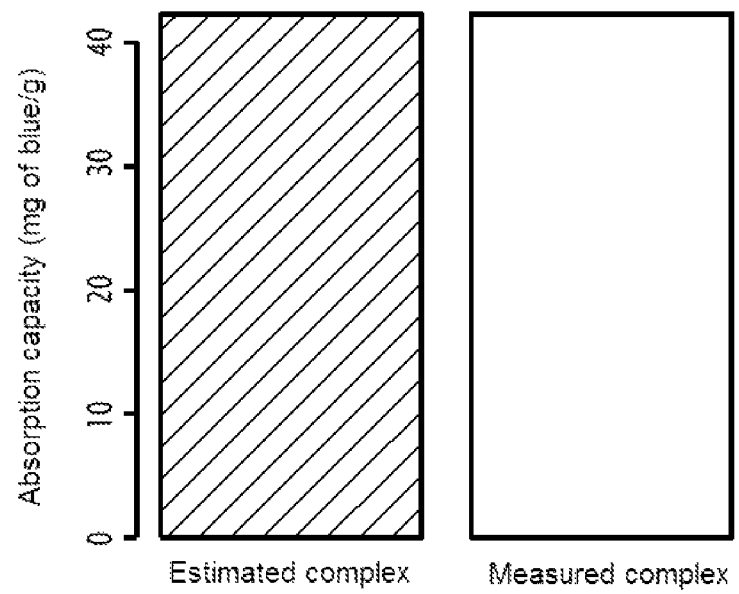

3 g of beepollen-clay complex are homogenized in 20 mL of demineralized water. Successive additions of 1 mL of 10 g/L methylene blue solution are performed until saturation. Saturation corresponds to the moment when a blue halo is formed on the paper filter. The result is confirmed by repeating the test of the spot every minute for 5 minutes. At 12 mL of added blue, the halo slightly persists even after 25 minutes. This is the saturation volume. The blue value of the beepollen-clay complex is therefore 42.2 mg of blue/g of clay (FIG. 6).

These results show that the estimated adsorption capacity of the complex is compliant with the measured adsorbing power. Nevertheless, this test also shows that the blue halo initially visible disappears over time. This shows that exchanges occur between the beepollen and the clay.

Balance of the Synergies Between the Clay and the Beepollen

Being aware of the intrinsic properties of beepollen and of clay, the following properties of the beepollen/clay complex were established. The results greatly exceed the estimations and confirm the synergies exerted by the combination of the beepollen and of the clay.

The whole of the advantages (/estimations) is illustrated in the following table:

| | |
|---|---|
| ABSORPTION | +9.5% |
| Prevents dehydration of the beepollen grain | |
| RETENTION | +15% |
| May retain substances | |
| ADSORPTION | = |
| May retain active molecules and lactic ferments | |
| EXCHANGE CAPACITY | 200% |
| Promotes beepollen—clay exchanges | |
| LACTIC FERMENTS | ×9.5 |
| Increases the load of lactic bacteria | |
| FUNGI | /3 |
| Reduces the formation of fungi | |
| | Greater effect/estimations |

Synergy of the beepollen/clay complex

These characteristics confirm the extremely interesting properties of the complex since the characteristics of beepollen are preserved and certain contributions such as that of lactic ferments are potentialized. The retention capacities will also allow addition of new molecules/substances which will be adsorbed by the complex.

Examples 1 and 2 were repeated with other types of clays: kaolinites, illites, fibrous minerals.

The results are summarized in the following table:

|  | Representative clay | Absorption | Retention | Adsorption | Exchange capacity | Lactic ferments | Fungi |
|---|---|---|---|---|---|---|---|
| Kaolinites | Kaolin | +11% | +1% | = | 20% | ×3 | /1.3 |
| Illites | Illite | +12% | +2% | = | 55% | ×2.5 | /1.2 |
| Smectites | Montmorillonite | +9.5% | +15% | = | 200% | ×9.5 | /3 |
| Chlorites or fibrous minerals | Attapulgite | +17% | +5% | = | 240% | ×3.5 | /1.5 |

EXAMPLE 3

Preparation of a Gelatin Capsule

A capsule with a hard casing, or gelatin capsule, including a prefabricated casing consisting of two cylindrical portions open at one end and the bottom of which is hemi-spherical, was prepared. The complex in solid form (powder or granules) is introduced into one of the two portions, and the second one is then fitted on to the first. The capsules Vcaps®, marketed by Pfizer, were used for this purpose. The skin of the gelatin capsule is hypromellose, certified to be without starch, without gluten and without preservatives.

The gelatin capsule comprises 500 mg of the beepollen/clay complex according to Example 1 per gelatin capsule. Illustratively, a gelatin capsule may comprise:
- clay: more than 50% by weight
- beepollen: 25% to 50% by weight
- hypromellose: 10% to 25% by weight
- titanium dioxide: 0.1% to 1%
- copper and chlorophyllin complex: less than 0.1% by weight.

All these ingredients are compliant with the use within the scope of a food supplement.

EXAMPLE 4

Characterization of the Gelatin Capsules

- energy value: 129 kcal/100 g
- lipids: 1.97%
- carbohydrates: 21.4%
- proteins: 6.42%
- ash: 62%.

The physical characteristics were also determined:.
- grain size: 500 µm;
- foreign bodies: absent.

The following chemical characteristics were obtained:
- pesticides, heavy metals, nitrites and nitrates: compliant with the European regulations in effect
- pH: not applicable
- humidity: 7.13%
- water activity wa: 0.675 at 24.4° C.
- viscosity: not applicable
- density: not applicable.

The invention claimed is:

1. A combination consisting of:
beepollen and clay, in the form of a beepollen/clay complex formed by mechanical mixing and passing the mixture through a sieve having a predetermined mesh size, in which, if stored without freezing, the properties of fresh beepollen are preserved after storage without freezing when compared to uncomplexed beepollen.

2. The combination according to claim 1, such that the clay is selected from clays of the kind: kaolinites, smectites, illites and chlorites or fibrous minerals.

3. The combination according to claim 1, such that the clay is montmorillonite.

4. The combination according to claim 1, comprising:
from 4% to 90% of beepollen;
from 10% to 96% of clay; and
the percentages being understood by weight.

5. The combination according to claim 1, comprising:
from 20% to 40% of beepollen; and
from 60% to 80% of clay.

6. The combination according to claim 1, such that it has a grain size of less than 500 µm, a humidity level of less than 15% and/or a water activity (wa) of less than 0.75.

7. A method for preparing a combination according to claim 1, comprising:
mechanically mixing beepollen and clay; and then passing the mixture through a sieve having a predetermined mesh size, whereby the properties of fresh beepollen are preserved after storage and without freezing compared to uncomplexed beepollen.

8. A pharmaceutical composition comprising:
a combination according to claim 1, and optionally one or several pharmaceutically acceptable excipients.

9. A method for treating osteoporosis, cardiovascular diseases, cancers, liver and metabolism disorders, circulatory disorders, menopausal symptoms, disorders of the nervous system, disorders of the gastrointestinal system, ocular disorders, fatigue, articular disorders, urinary disorders, prostate disorders, nutritional disorders, dermatological and cosmetodermatological disorders and hydro-electrolytic imbalances including administering a combination according to claim 1.

10. A food composition comprising:
a combination according to claim 1.

11. A gelatin capsule containing a combination of clay and beepollen according to claim 1.

12. A drug comprising as a carrier, a combination of clay and of beepollen according to claim 1.

13. A method according to claim 9 wherein the method is for treating prostate disorders that is benign hypertrophia of the prostate, chronic prostatitis, prostatodynia and prostate cancer.

14. A method of treatment during convalescence or post-surgery comprising administering a combination of claim 1.

15. A method of improving in physical conditions comprising administering a combination of claim 1.

\* \* \* \* \*